(12) United States Patent
Schmid et al.

(10) Patent No.: US 7,628,808 B2
(45) Date of Patent: Dec. 8, 2009

(54) DEVICE FOR CONNECTING A CARDIAC BIVENTRICULAR ASSIST MEANS

(75) Inventors: Thomas Schmid, Gilching (DE); Wolfgang Schiller, Bonn (DE)

(73) Assignee: Deutsches Zentrum fur Luft und Raumfahrt E.V., Cologne (DE)

( * ) Notice: Subject to any disclaimer, the term of this patent is extended or adjusted under 35 U.S.C. 154(b) by 502 days.

(21) Appl. No.: 10/911,539

(22) Filed: Aug. 5, 2004

(65) Prior Publication Data
US 2005/0209502 A1    Sep. 22, 2005

(30) Foreign Application Priority Data
Mar. 22, 2004    (DE) ........................ 10 2004 014 337

(51) Int. Cl.
*A61M 1/10* (2006.01)
(52) U.S. Cl. ..................................... 623/3.26
(58) Field of Classification Search .................... 600/16, 600/17; 623/3.1, 3.11, 3.26, 3.3, 3.29, 1.65
See application file for complete search history.

(56) References Cited
U.S. PATENT DOCUMENTS

| 3,766,567 A | | 10/1973 | Kahn et al. |
| 4,619,643 A | * | 10/1986 | Bai ............................. 604/43 |
| 4,682,978 A | * | 7/1987 | Martin ......................... 604/43 |
| 4,955,856 A | * | 9/1990 | Phillips ........................ 600/16 |
| 5,032,128 A | * | 7/1991 | Alonso ....................... 623/2.41 |
| 5,135,539 A | | 8/1992 | Carpentier |
| 5,743,845 A | * | 4/1998 | Runge .......................... 600/16 |
| 6,293,969 B1 | * | 9/2001 | Chuter ....................... 623/1.16 |
| 6,576,009 B2 | * | 6/2003 | Ryan et al. ................. 623/1.35 |
| 6,610,088 B1 | * | 8/2003 | Gabbay ...................... 623/2.38 |
| 6,802,806 B2 | * | 10/2004 | McCarthy et al. ............. 600/16 |
| 7,172,625 B2 | * | 2/2007 | Shu et al. ................... 623/2.41 |
| 2002/0082467 A1 | * | 6/2002 | Campbell ..................... 600/16 |
| 2002/0165426 A1 | * | 11/2002 | Sporer et al. .................. 600/16 |
| 2005/0113905 A1 | * | 5/2005 | Greenberg et al. ......... 623/1.16 |

FOREIGN PATENT DOCUMENTS

DE    10217635 A1 *  11/2002

* cited by examiner

*Primary Examiner*—George R Evanisko
*Assistant Examiner*—Amanda Patton
(74) *Attorney, Agent, or Firm*—Browdy and Neimark, P.L.L.C.

(57) ABSTRACT

For connecting a cardiac biventricular assist means including a dual-chamber pumping device, and an electrically powered compressor means provided between the two chambers (12, 15) a partially flexible one-part or multi-part adapter (20) is provided with two through-passageways (21, 22; 34, 35) each separate from the other, said adapter being securely held, on the one hand, in a port (4*a*) in the apical portion of the septum (4) and, on the other, in a port (2*a*) in/at the apex of the left ventricle (2) so that the through-passageway (22; 35) extending into the left ventricle (2) is connected directly or by means of a first flexible tube (11) to the inlet (12*a*) of the one chamber (12) and the other through-passageway (21; 34) extending into said right ventricle (3) is connected directly or by means of a second flexible tube (14) to the inlet (15*a*) of the other chamber (15).

11 Claims, 6 Drawing Sheets

Fig.9
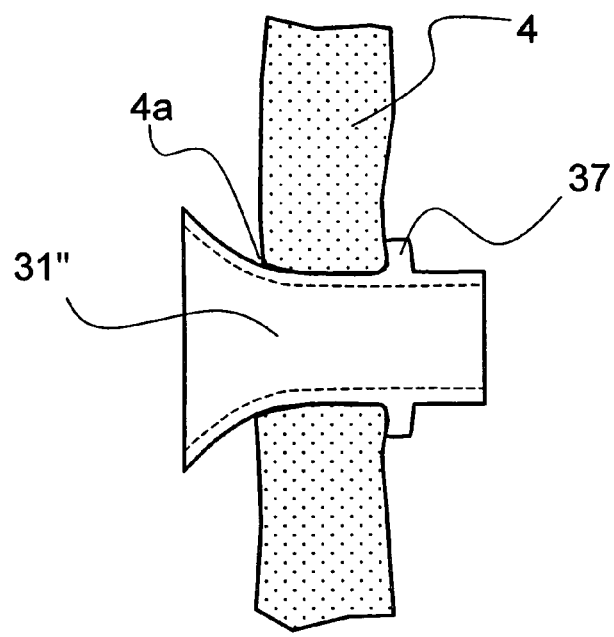
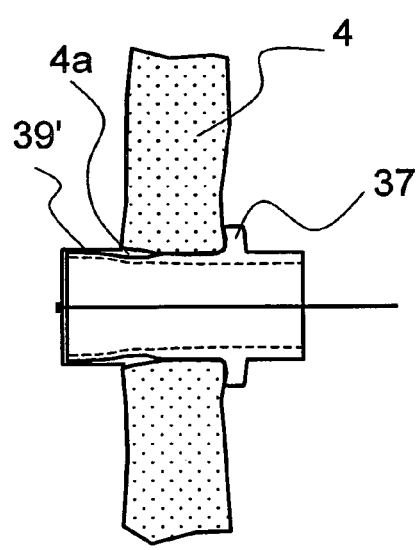
Fig.10a
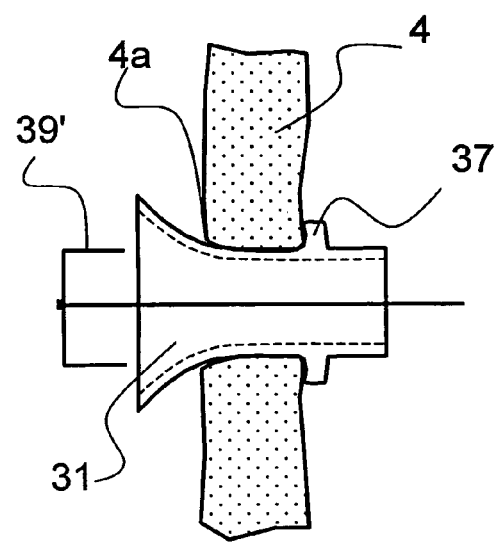
Fig.10b

DEVICE FOR CONNECTING A CARDIAC BIVENTRICULAR ASSIST MEANS

FIELD OF THE INVENTION

The invention relates to a device for connecting a cardiac biventricular assist means including a dual-chamber pumping device, the chambers of which each comprise an inlet and an outlet including cardiac valve prostheses, the outlet of the one chamber being connected to the aorta and the outlet of the other chamber being connected to the pulmonary artery, and featuring an electrically powered compressor means provided between the two chambers.

BACKGROUND OF THE INVENTION

Cardiovascular diseases have since become the number one fatality in western industrial nations with ishemic heart disease and heart failure being the most frequent causes of death in Germany. Of a total of 2.7 million in in-patient treatment for cardiovascular diseases, roughly 15% die.

Implantable mechanical ventricular assist devices (VAD) have been in use now clinically for some 15 years. This form of therapy mainly serves as a bridge to transplant when no donor organ is available or the patient is already in such a critical health condition that he would in all probability fail to survive the acute stress of a heart transplantation and the initial high-dosis immune suppressive therapy involved. Then, following stabilization over several months by a VAD with an improvement in the organ functions detrimented previously by acute or chronic diminished circulation, the patients can be admitted to heart transplantation with a higher anticipated success.

More recent results have shown that the functioning of the heart may be improved by this therapy to such an extent that there is a possibility of system explantation without a subsequent heart transplantation (bridge to recovery). A future aim with assist systems of enhanced reliability is to allow them to remain in the body as an alternative to transplant (ATT).

Due to the lack of donors and organ allocation in accordance with a waiting list early or, in some cases, premature application for transplantation is experienced which results in suboptimal organ allocation. By making use of suitable heart assist systems on a full-scale basis available donor organs could be optimally allocated by eliminating a waiting time calculation and the result of the heart transplantation could be improved on recovery of the organ functioning following mechanical ventricular assistance.

Since no fully implantable, biventricular assist system is hitherto available, only extracorporal systems for assisting biventricular failure could hitherto find application. Left ventricular assist systems are built as a rule with a pump chamber.

Currently, the only way of assisting both ventricles is with a total artificial heart (TAH) which, however, is too big to be additionally implanted as an assist system. Instead, the native heart in this case would have to be totally removed, resulting in no back-up being available should the artificial system fail. This therapy also eliminates the bridge to recovery (BTR) option since the heart has been removed. Experience has furthermore shown that it is easier to make the transplantation when the patient had the supply of an assist system than when a total artificial heart (TAH) was implanted.

Problematic in a biventricular assist is making the connection to the right ventricle because of its thin muscle tissue. Hitherto this connection was made via anastomosis to the right atrium. Since the tissue here too is relatively thin, haemorrhage complications may arise should the suture rupture. On top of this, there is the danger of the atrium collapsing on blood intake due to an assist system.

SUMMARY OF THE INVENTION

The objective of the invention is to apply a device for connecting a cardiac biventricular assist means to both ventricles safely and durably.

Since the right ventricle is not required to produce such a high pressure as the left ventricle which needs to pump the blood via the aorta throughout all of the body, the muscle tissue of the right ventricle is weaker than that of the left ventricle.

This is why, in accordance with a first embodiment of the invention a one-part or multi-part adapter flexible at least in part is provided with two through-passageways each separate from the other, the adapter being securely held, on the one hand, in a port in the apical portion of the septum and, on the other in a port in/at the apex of the left ventricle so that the through-passageway extending into the left ventricle is connected directly or by means of a first flexible tube to the inlet (12a) of the one chamber of a dual-chamber pumping device and the other through-passageway extending into the right ventricle is connected directly or by means of a second flexible tube to the inlet of the other chamber.

In this arrangement any suitable dual-chamber assist system can be used in conjunction the invention, also suitable being the compact system to assist the left ventricle adapter as it reads from DE 102 17 635 A1. How this system is modified to permit its application as a biventricular assist system in accordance with the invention will now be described in detail.

In accordance with one advantageous aspect of the invention the one-part adapter (20) comprises a flexible, funnel-shaped portion contacting the septum on the right following application of the adapter into the port thereof, a circumferential bead in full contact with the septum on the right following application of the adapter, and a receiving portion with the two through-passageways porting into the two ventricles. In addition, a displaceable, sleeve-shaped locking ring is provided outside of the left ventricle on the receiving portion.

Each of the two through-passageways in the receiving portion of the adapter may have an approximately semi-circular cross-section. Furthermore, in accordance with the invention, the outer sides of the one-part adapter, especially the funnel-shaped portion, the circumferential bead and part of the receiving portion may be covered with tissue material at least in part.

In accordance with a further preferred embodiment a multi-part adapter comprises an insertion part, a funnel-shaped portion, a receiving part having a bead at the one end and two through-passageways extending into the left and right ventricle respectively to which the corresponding inlet of the chambers is connected directly or by means of flexible tubes. Furthermore, a beadlike tissue band is provided for sliding on the receiving part. In addition, the funnel-shaped insertion part in accordance with the invention may also feature a circumferential collar.

For locating the funnel-shaped insertion part in the receiving part of the multi-part adapter a sawtooth profile may be configured on both parts, preferably on the outer side of the insertion part. Furthermore in accordance with the invention both the insertion part and the receiving part may be covered outwardly at least in part by tissue material.

When a flexible tube is stapled by a conventional suture stapler to the atriums, for example to the right atrium, to one or both of the ventricles, arteries and other suitable locations, and blood needs to be removed, an adapter version in accordance with the invention is applied in a flexible tube to optimise the flow whilst the adapter stabilizes the vessel port. In this arrangement, depending on the version of the suture stapler involved, the flexible tube is stapled to the corresponding vessel and the necessary port incised, for example, through the wall of the vessel in the apex of the left ventricle or right atrium. However, the remaining projection protruding inwardly (into the lumen) constitutes a major thrombosis risk. This is because the blood taken from the corresponding vessel recirculates behind the bead-like projection or becomes totally stationary in thus constituting an added thrombosis risk.

In addition, it is to be noted that the flexible tubes provided for such connections are generally incapable of maintaining a port open in strong muscle tissue, such as for example in the tissue of the left ventricle. To prevent such a closure or at least a restriction in the port provided in the vessel, a correspondingly rigid or at least partly rigid adapter in accordance with the invention is inserted by means of which, for one thing, the port is maintained open to the desired degree and thus stabilized and, for another, an optimal flow is assured.

Such a rigid or at least partly rigid adapter inserted into the flexible tube comprises in accordance with an advantageous aspect of the invention a portion featuring a funnel-shaped port translating into a circular cylindrical hollow portion. Furthermore, the adapter in accordance with the invention is configured outwardly as a stepped circular cylinder so that on application of this adapter to a tube stapled to a vessel a step of the stepped circular cylinder protruding inwardly comes into full contact with the projection. To improve a connection between the projection and the step of the stepped circular cylinder both can be adhesively bonded together.

To secure the adapter in place axially a sleeve can be press-mounted outwardly on to the flexible tube and on the adapter inserted therein. However, this sleeve may also be held in place by other means mechanically on the inserted adapter or connected to the latter.

BRIEF DESCRIPTION OF THE DRAWINGS

The invention will now be detailed with reference to the drawings in which:

FIG. 9 is a diagrammatic illustration, not to scale, of one variant of an applied insertion part;

FIGS. 10 and 10b are section views of an insertion aid for applying an insertion part including a funnel-shaped portion in the septum;

DETAILED DESCRIPTION OF THE INVENTION

Figure 1:
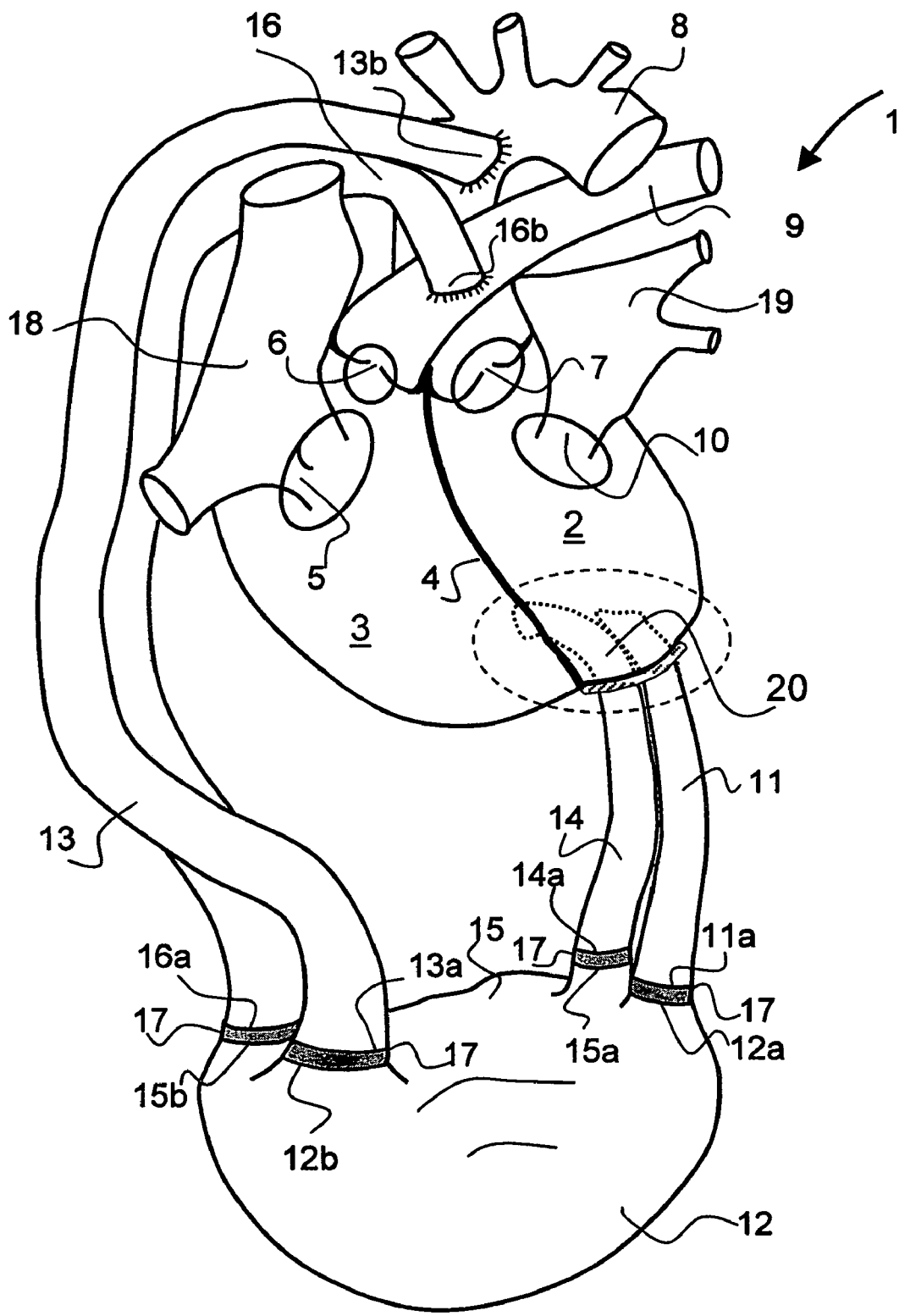
FIG. 1 is a diagrammatic illustration, not to scale, of a heart including a device indicated by the broken line for connecting a biventricular assist system.

Referring now to FIG. 1 there is illustrated pronounced diagrammatically a heart identified in its entirety by the reference numeral 1, comprising a left atrium 19, a left ventricle 2 as well as a right atrium 18 and a right ventricle 3. The left ventricle 2 is separated from the right ventricle 3 by a septum 4 formed of strong heart muscle tissue.

Provided between the two atriums 18 and 19 and the corresponding ventricles 3 and 2 are valves in the form of the tricuspid valve 5 and mitral valve 10 respectively. Illustrated furthermore diagrammatically between the left ventricle 2 and aorta 8 is the aortic valve 7 as well as between the right ventricle 3 and the pulmonary artery 9 leading to the lung is the pulmonary valve 6.

Illustrated below the heart 1 diagrammatically is a dual-chamber pumping device as detailed in DE 102 17 635 A1 of which only the two chambers are indicated in the drawing greatly simplified and diagrammatically, namely a chamber 12 and a chamber 15 arranged there behind in the drawing. The two chambers 12 and 15 each comprise inlets 12a and 15a as well as outlets 12b and 15b respectively.

Accommodated in the region of the inlets and outlets are the cardiac valve prosthetics 17 indicated shaded in the drawing. Secured to the outlets 12b and 15b of the two chambers 12 and 15 are the ends 13a and 16a of the two flexible tubes 13 and 16 respectively. The other ends 13b and 16b of the flexible tubes 13 and 16 are fixedly connected to the aorta 8 and pulmonary artery 9 respectively.

Secured to the inlet ports 12a and 15a of the chambers 12 and 15 are the ends 11a and 14a of a first flexible tube 11 and second flexible tube 14 respectively. The other ends (not shown) of the two flexible tubes 11 and 14 are secured to the corresponding ends of an adapter 20 indicated in FIG. 1 and framed by the broken line ellipse; this and further advantages will now be detailed with reference to the drawings.

Provided between the two chambers 12 and 15 of the dual-chamber pumping device is a compressor device shown and detailed in DE 102 17 635 A1 (not shown in the diagrammatic illustration of the drawing). As already indicated above the left ventricular assist system known from DE 102 17 635 A1 can be modified into a dual-chamber pumping device for cardiac biventricular assistant, substantially involving eliminating the Y-adapter through which in the left ventricular assistant system the inlets and outlets of the two pump chambers are ported together.

In addition, the section view provided in the Y-adapter at the outlet end is replaced by two conventional cardiac valve prosthetics 17, directly located in the outlet portions of the two chambers 12 and 15 of the dual-chamber pumping device. The compressor device provided in DE 102 17 635 A1 can be taken over substantially unchanged together with the drive unit assigned thereto as well as the further units provided for the drive unit.

Figure 2:
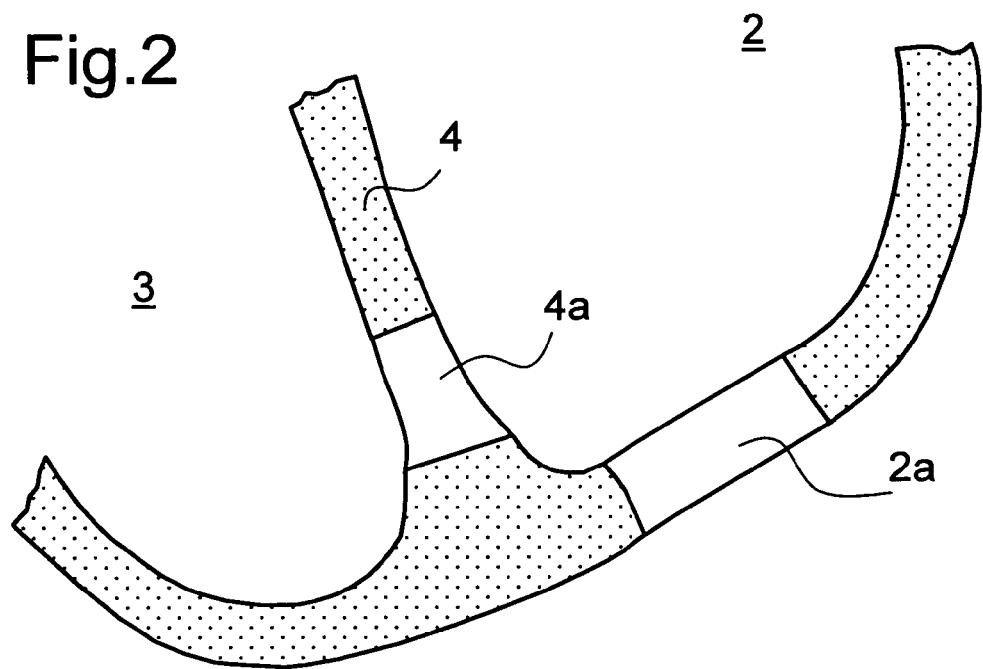
FIG. 2 is a section view through part of the apex of the left ventricle and the apical portion of the septum including the left ventricle.

Referring now to FIG. 2 there is illustrated in a diagrammatic section view, not to scale, the lower part of the apex of the left ventricle 2 including a port 2a provided therein, the apical part of the septum 4 with a port 4a provided therein as well as a apical part of the right ventricle 3.

Figure 3:
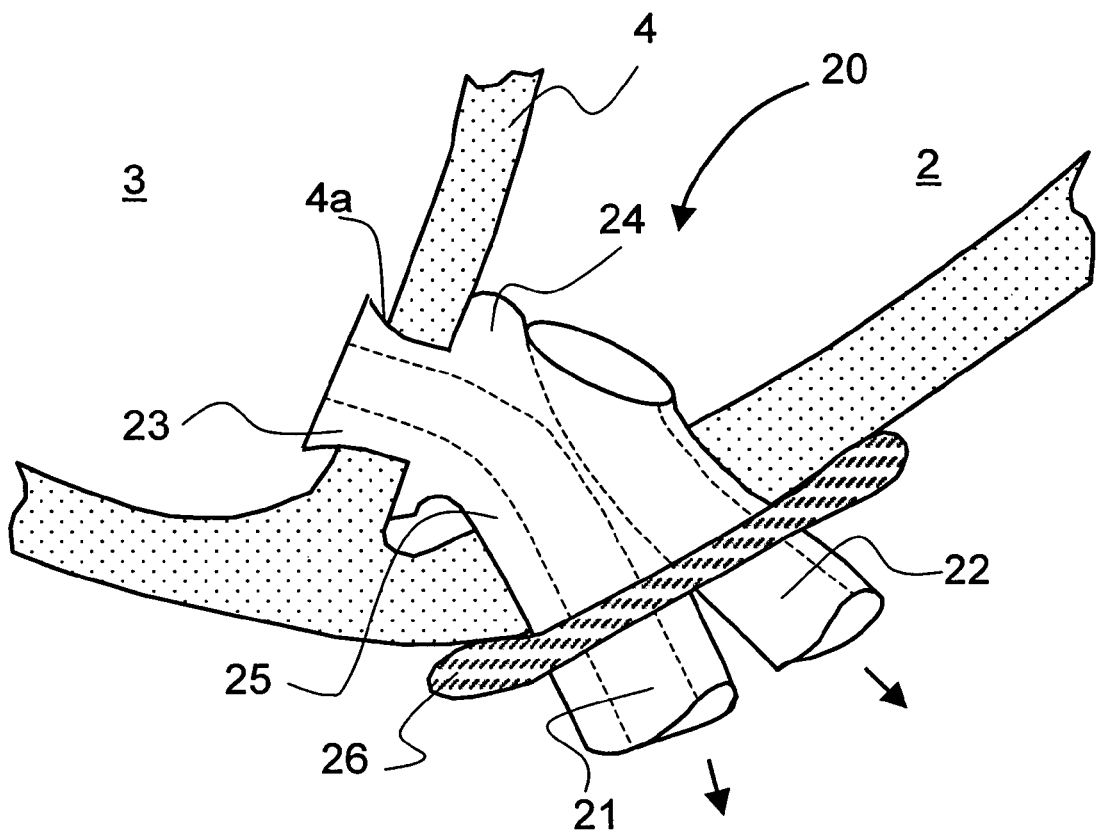
FIG. 3 is a diagrammatic illustration, not to scale, of an adapter inserted in both the septum and apex of the left ventricle.

Referring now to FIG. 3 there is illustrated in a diagrammatic view, not to scale, a one-part adapter identified in its entirety by the reference numeral 20 comprising an insertion portion 23 with a funnel-shaped port held in the port 4a of the septum 4 and connecting a receiving portion 25 curved preferably proximally. Configured in the adapter 20 are two separate, through-passageways 21 and 22, of which the first through-passageway 21 begins in the right ventricle 3 and ends at the other end in the flexible tube 14 (FIG. 1) not shown in FIG. 3, whilst the second through-passageway 22 begins in the apex of the left ventricle 2 and ends in the flexible tube 11 likewise not shown in FIG. 3. The two flexible tubes 11 and 12 are, as shown in FIG. 1, connected to the inlets 12a and 15a of the two chambers 12 and 15 respectively of the dual-chamber pumping device, although the one-part adapter 20 may also be configured so that the through-passageways can be directly connected to the aforementioned inlets 12a and 15a.

Figure 4:
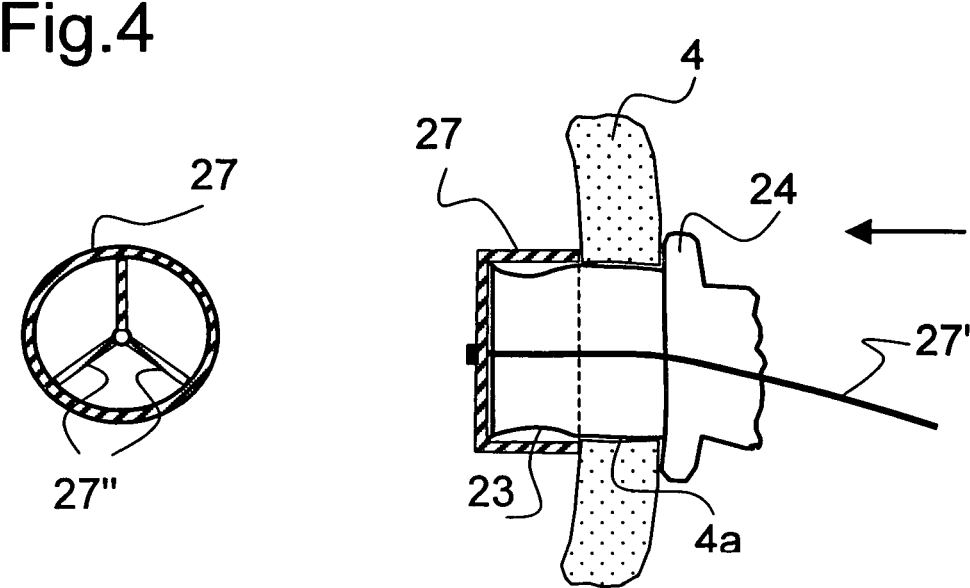
FIG. 4 is a diagrammatic illustration of an insertion aid for applying an adapter to the septum, shown in a plan view and section view.

Referring now to FIG. 4 there is illustrated how for application of the funnel-shaped insertion part 23 of the adapter 20 in the port 4a of the septum 4 an insertion aid in the form of a flexible circular cylindrical cap 27 is fitted to the funnel-shaped portion, resulting in the funnel-shaped insertion portion 23 being deformed as shown in FIG. 4. The insertion aid 27 with the deformed funnel-shaped portion 23 of the adapter is inserted in the direction of the arrow as shown in FIG. 4 through the port 4a in the septum 4 until it is in position as shown in FIG. 4.

For example, by means of the relatively rigid wire 27' movingly attached to the bottom of the cap reinforced by ribs 27", the cap 27 is shifted down from the deformed insertion portion 23, resulting in the flexible funnel-shaped insertion portion 23 flaring to press against the septum 4 on the left by its own tension, as indicated in FIG. 3. This ensures a good seal as regards port 4a whilst locating the adapter axially as regards the septum. After a time, the insertion portion 23 of the adapter fuses with the tissue of the septum 4. Since the insertion aid in the form of the cap 27 is movingly connected to the rigid wire 27' it can also be retrived from the right ventricle 3 through the through-passageway 21.

The outer sides of the adapter 20, particularly of the funnel-shaped insertion portion 23, the circumferential bead 24 as well as part of the outer surface area of the receiving portion 25 may be expediently covered with tissue material. The ends of the one-part adapter 20 protruding outwardly from the left ventricle 2 should be chamfered to create a neat transition between the adapter 20 and the applied flexible tubes 11 and 14 or inlets 12a and 15a respectively. This prevents deposits materializing in the interface between the adapter 20 and flexible tubes 11, 14 or inlets 12a, 15a respectively. The one-part adapter 20 as well as more particularly the flexible, funnel-shaped portion may be made of a plastics material or of metal, for example nitinol, a material which expands in response to warmth.

Referring now to FIG. 3 again there is illustrated how a shiftable locking ring 26 of tissue material is provided to permit adapting to the differences in the wall thickness at the apex of the left ventricle 2. When, as indicated in FIG. 2, the portion protruding outwardly from the port 2a is circular, the locking ring 26 may be, for example, a tapped sleeve covered with tissue material for screwing onto the one-part adapter 20 from without.

Figure 5:
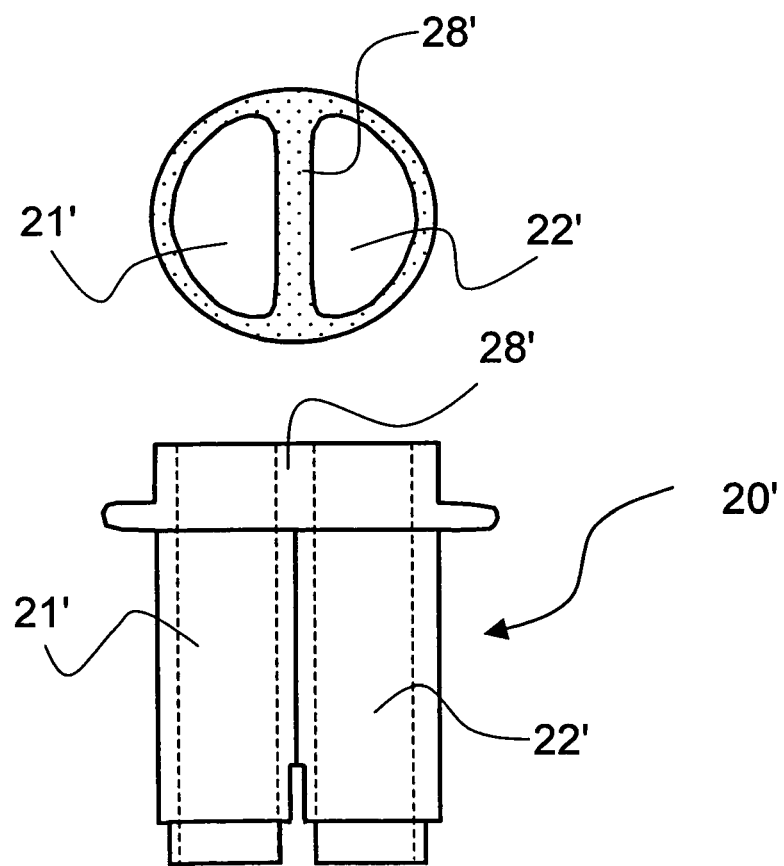
FIG. 5 is a plan view and proximal view of a further embodiment of a one-part adapter.

Referring now to FIG. 5 there is illustrated how the two through-passageways 21' and 22' may be configured semi-circular in cross-section, the transitions to the middle web 28' being rounded to prevent deposits in this area. The variant as shown in FIG. 5 is in addition compact in facilitating it being sealed in the port 2a.

Figure 6:
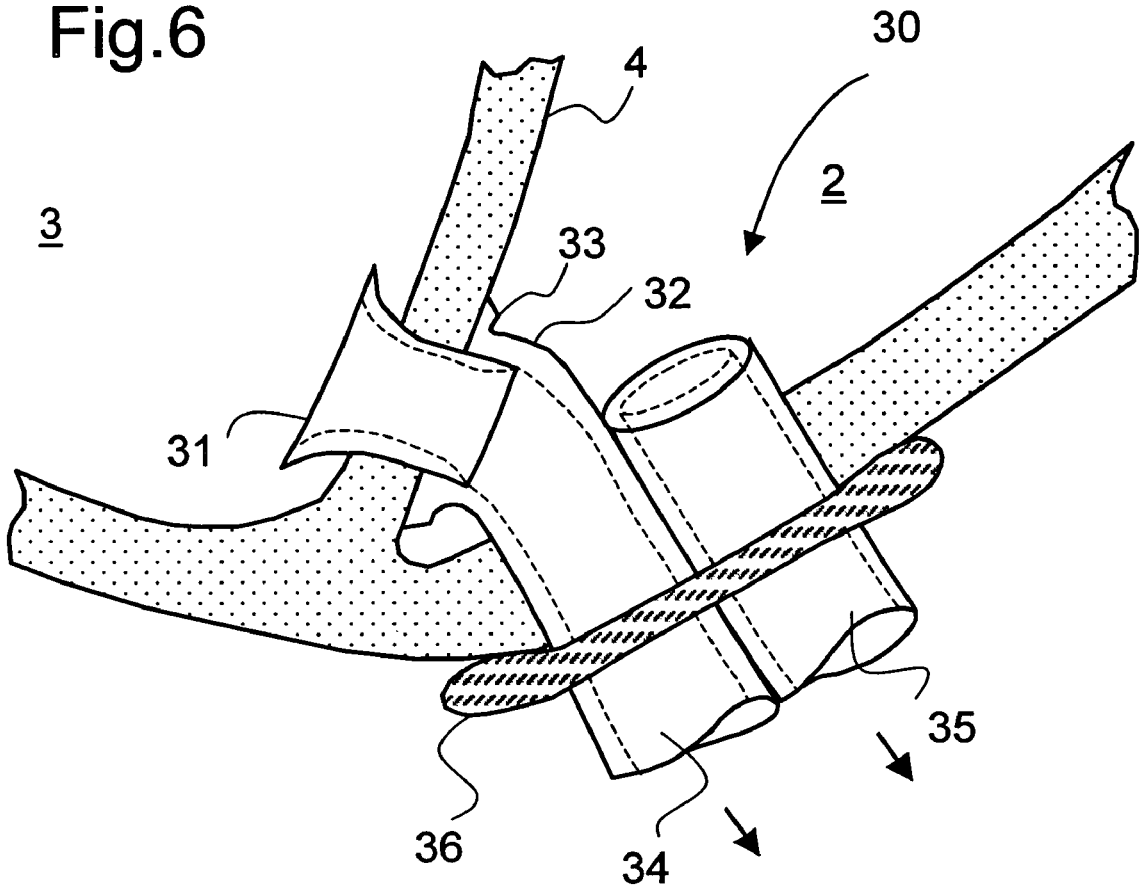
FIG. 6 is a diagrammatic illustration, not to scale, of a multi-part adapter inserted in the septum and apex of the left ventricle.
Figure 8A:
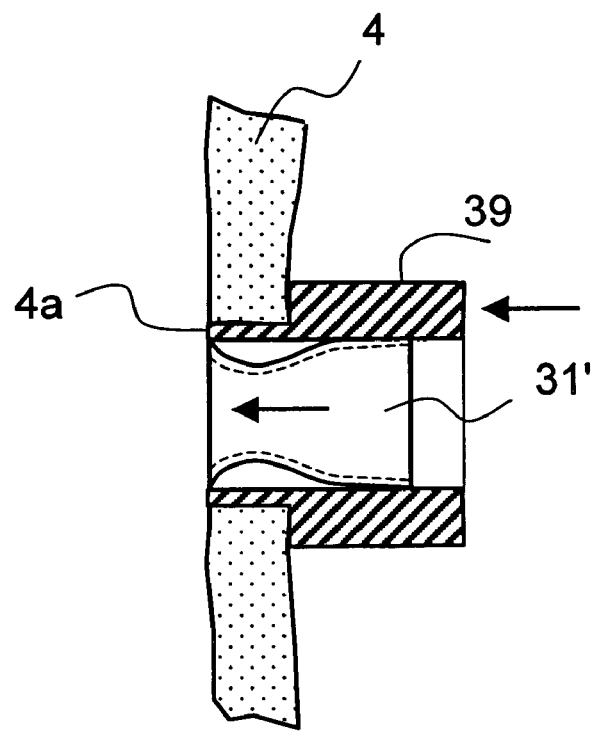
FIGS. 8a and 8b are views of an insertion aid for applying an insertion part.
Figure 8B:
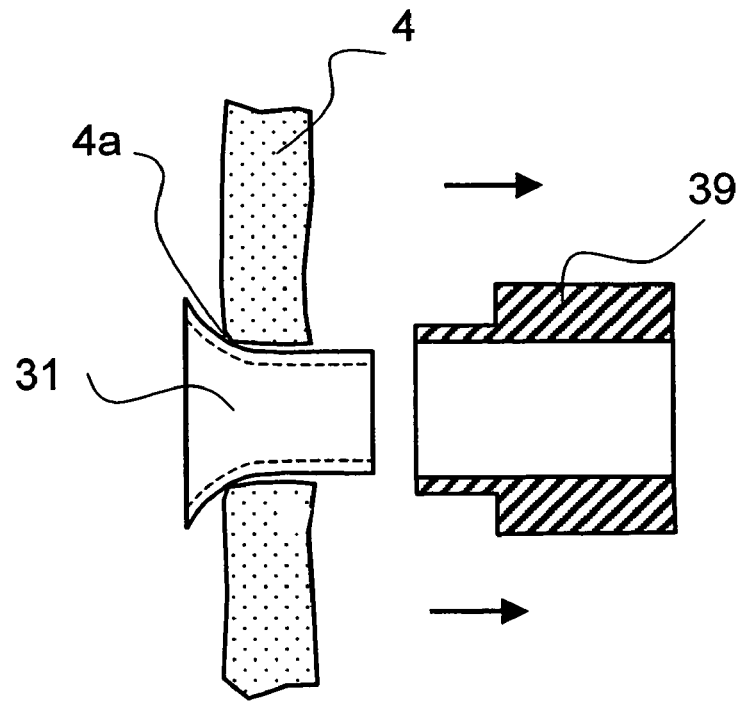

Referring now to FIG. 6 there is illustrated a multi-part adapter configured partly flexible as identified in its entirety by the reference numeral 30. The adapter 30 comprises a flexible insertion part 31 including a funnel-shaped port which as indicated by the arrow in FIGS. 8a and 8b is insertable by means of an insertion aid in the form of a stepped cylindrical sleeve 39 in the direction of the arrow through the port 4a in the septum 4. Once the insertion part 31 is inserted in the port 4a the insertion aid 39 is removed in the direction of the arrow. After this, a receiving part 32 curved preferably at the proximal end is inserted through the port 2a in the apex of the left ventricle 2 and applied to the end of the right ventricle 3 protruding into the right ventricle 3 until a bead 33 formed at the receiving portion comes into contact with the septum 4 on the right.

To locate the receiving part 32 in the funnel-shaped insertion part 30 a sawtooth profile is configured on both parts, preferably on the outer side of the receiving part 32. The receiving part 32 features in turn two through-passageways 34 and 35 respectively. The through-passageways 34 and 35 are in turn connectable either by means of flexible tubes 11 and 14 or by correspondingly dimensioning the receiving part 32 also directly to the inlets 12a and 15a of the chambers 14 and 15 respectively of the dual-chamber pumping system. The two arrows as shown in FIG. 6 indicate the direction in which the blood flows from the corresponding ventricle.

Figure 7:
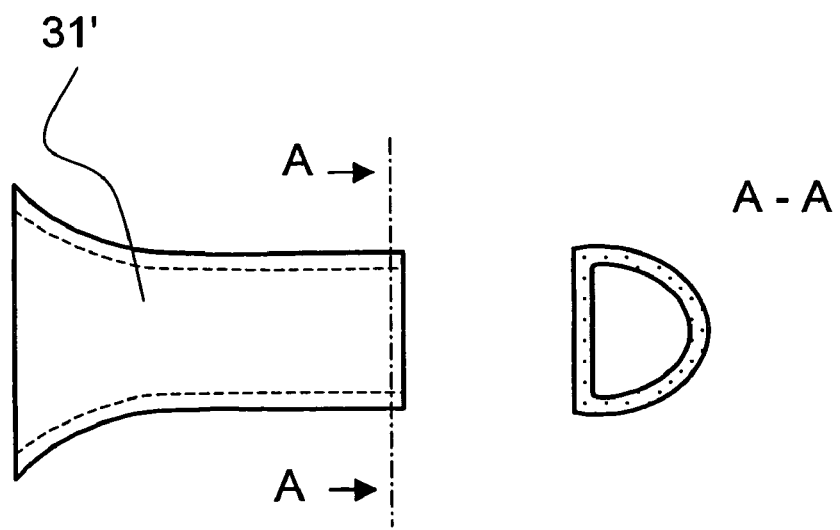
FIG. 7 is a side view and section view of an insertion part for a multi-part adapter.

Referring now to FIG. 7 there is illustrated an insertion part 31' configured with a semi-circular cross-section as evident from the section view A-A.

Referring now to FIG. 9 there is illustrated a variant of a funnel-shaped insertion part 31" which differs from the insertion part 31' described above by a circumferential collar 37 being additionally provided for coming into contact with the septum 4 on the right after the insertion part 31" has been inserted through the port 4a by means of the insertion aid 39' (see FIGS. 10a and 10b). The insertion aid 39' has substantially the same configuration and function as the insertion aid 27 already described with reference to FIG. 4

LIST OF REFERENCE NUMERALS 1 heart
2 left ventricle
2a port in 2
3 right ventricle
4 septum
4a port in 4
5 tricuspid valve
6 pulmonary valve
7 aortic valve
8 aorta
9 pulmonary artery
10 mitral valve
11, 11' flexible tube
11a,b ends of 11
12 pump chamber
12a inlet
12b outlet of 12
13 flexible tube
13a,b ends of 13
14,14' flexible tube
14a,b ends of 14
15 pump chamber
15a inlet of 15
15b outlet of 15
16 flexible tube
16a,b ends of 16
17 cardiac valve prosthetics
18 right atrium
19 left atrium
20, 20' one-part adapter 21, 22 through-passageway
21', 22' through-passageway with semicircular section
23 portion with funnel-shaped port
24 circumferential bead
25 receiving portion
26 locking ring
27 insertion aid (circular flexible cap)
27' rigid wire
27" stiffener web
28' middle web of 20
30 multi-part adapter
31, 31', 31" insertion aid with funnel-shaped port
32 receiving part
33 bead on 32
24, 35 through-passageway
36 tissue band
37 circumferential collar on 31
39 sleeve
39' flexible cap

What is claimed is:

1. A system comprising:
a multi-part adapter (30); and
a cardiac biventricular assist device,
wherein the multi-part adapter (30) is adapted to be implanted in a first opening (4a) in an apical region of a septum (4) and a second opening (2a) in the apex of a left ventricle (2) of a heart of a patient and is connected to the cardiac biventricular assist device of a patient when implanted, the cardiac biventricular assist device having a two-chamber pumping device, the two chambers (12; 15) of which each comprise an inlet (12a; 15a) and an outlet (12b; 15b) including cardiac valve prosthetics (17) provided therein, and an electrically powered compressor means provided between the two chambers (12, 15),
the multi-part adapter (30) comprises:
a flexible insertion part (31) formed as a unit having a first end and a second end with a passageway therebetween;
wherein a funnel-shaped portion is formed on the first end and the second end is adapted to extend through the first opening (4a);
a receiving portion (32) formed as a unit having a first separate through passageway (34) having an opening at a first end and a second end engaged to the inlet (12a, 15a) of one of the two chambers (11, 15) of the pumping device and a second separate through passageway (35) which is shorter than the first through passageway having an open first end adapted to terminate in the left ventricle and a second end engaged to the inlet (12a, 15a) of the other of the two chambers (12, 15) of the pumping device;
wherein a portion of a length of a wall of the second separate through passageway is abuttingly fixed to a wall of the first separate through passageway up to the first end of the second through passageway;
wherein the fixed first and second separate through passageways is adapted to extend through and abut against the second opening (2a);
a circumferential collar (33) formed as a unit with and at the first end of the first separate through passageway (34) which has two sides that project out from the circumference of the first separate through passageway, and
wherein the opening of the first end of the first separate through passageway is fixed to and over the second end of the insertion part extending through the first opening (4a) so that the circumferential collar is adapted to abut the septum (4), and fix the end of the first separate through passageway and the funnel shaped portion of the insertion part to the septum and engage the passageway of the insertion part to the first separate through passageway.

2. The adaptor according to claim 1, wherein the second ends of the first and second through passageways are spaced apart from each other and respectively fixed on said inlets of the two chambers.

3. The adaptor according to claim 1, wherein the second ends of the first and second through passageways are spaced apart from each other and respectively engaged on said inlets of the two chambers by a flexible tube.

4. The adaptor according to claim 1, wherein both the insertion part (31) and the receiving portion (32) are made in their entirely of a plastic.

5. The adaptor according to claim 1, wherein both the insertion part (31) and the receiving portion (32) are made in their entirety of a metal.

6. The adapter as set forth in claim 1, further comprising a sawtooth profile on the first end of the receiving part (32) for fixing the flexible insertion part (31; 31').

7. The adapter as set forth in claim 1, wherein both the insertion part (31, 31') and the receiving part (32) are outwardly covered in part by tissue material.

8. The adapter as set forth in claim 1, wherein the two separate through passageways (34, 35) of the adapter (30) each have an approximately semi-circular cross-section.

9. The adapter according to claim 1, wherein a tissue band (36) is adapted to secure the adapter (30) to the apex of the left heart ventricle (2).

10. The adapter according to claim 1, wherein the first and second through passageways (34,35) are formed as a unit along lengths thereof so that one of the passageways communicates with the right heart ventricle and the other of the passageways communicates with the left heart ventricle.

11. A stem comprising:
a multi-part adapter (30); and
a cardiac biventricular assist device,
wherein the multi-part adapter (30) is adapted to be implanted in a first opening (4a) in an apical region of a septum (4) and a second opening (2a) in the apex of a left ventricle (2) of a heart of a patient and is adapted to be connected to the cardiac biventricular assist device of a patient when implanted, the cardiac biventricular assist device having a two-chamber pumping device, the two chambers (12; 15) of which each comprise an inlet (12a; 15a) and an outlet (12b; 15b) including cardiac valve prosthetics (17) provided therein, and an electrically powered compressor means provided between the two chambers (12, 15),
the multi-part adapter (30) comprises:
an insertion part (31) formed as a unit having a first end and a second end with a passageway therebetween;
wherein a funnel-shaped portion is formed on the first end and the second end is adapted to extend through the first opening (4a);
a receiving portion (32) formed as a unit having a first separate through passageway (34) having an opening at a first end and a second end adapted to be engaged to the inlet (12a, 15a) of one of the two chambers (11, 15) of the pumping device and a second separate through passageway (35) which is shorter than the first through passageway having an open first end adapted to terminate in the left ventricle and a second end adapted to be engaged to the inlet (12a, 15a) of the other of the two chambers (12, 15) of the pumping device;

wherein a portion of a length of a wall of the second separate through passageway is abuttingly fixed to a wall of the first separate through passageway up to the first end of the second through passageway;

wherein the fixed first and second separate through passageways is adapted to extend through and abut against the second opening (2a);

a circumferential collar (33) formed as a unit with and at the first end of the first separate through passageway (34) which has two sides that project out from the circumference of the first separate through passageway, and wherein the opening of the first end of the first separate through passageway is fixed to and over the second end of the insertion part extending through the first opening (4a) so that the circumferential collar is adapted to abut the septum (4), and fix the end of the first separate through passageway and the funnel shaped portion of the insertion part to the septum and engage the passageway of the insertion part to the first separate through passageway, and wherein the multi-part adapter is rigid to prevent a closure or restriction of the passageways when connecting to the first opening (4a) and the second opening (2a) of the heart.

* * * * *